United States Patent [19]

Platz et al.

[11] Patent Number: 4,550,195
[45] Date of Patent: Oct. 29, 1985

[54] MANUFACTURE OF PENT-3-ENOIC ACID AND ITS ALKYL ESTERS

[75] Inventors: Rolf Platz, Mannheim; Rudolf Kummer, Frankenthal; Heinz-Walter Schneider; Kurt Schwirten, both of Ludwigshafen, all of Fed. Rep. of Germany

[73] Assignee: BASF Aktiengesellschaft, Fed. Rep. of Germany

[21] Appl. No.: 295,088

[22] Filed: Aug. 21, 1981

Related U.S. Application Data

[63] Continuation of Ser. No. 805,416, Jun. 10, 1977, abandoned.

[51] Int. Cl.$^3$ .............................................. C07C 67/38
[52] U.S. Cl. .................................................. 560/206
[58] Field of Search ................... 560/206, 207, 233; 562/522

[56] References Cited

U.S. PATENT DOCUMENTS

| | | | |
|---|---|---|---|
| 2,448,368 | 8/1948 | Gresham et al. | 562/522 |
| 3,462,481 | 8/1969 | Rudkovsky et al. | 562/497 |
| 3,694,502 | 9/1972 | Keblys et al. | 562/522 |

OTHER PUBLICATIONS

Matsuda, Akio et al., *Bull. Chem. Soc. Japan*, vol. 38, (1965), pp. 710–715.
Matsuda, Akio, Ibid., vol. 46, (1973), pp. 524–530.
Matsuda, Akio et al., *Chemical Abstracts*, vol. 82, (1975), #58,475t.

*Primary Examiner*—Natalie Trousof
*Assistant Examiner*—L. Hendriksen
*Attorney, Agent, or Firm*—Keil & Weinkauf

[57] ABSTRACT

A process for the manufacture of pent-3-enoic acid and its alkyl esters, of the general formula

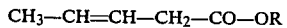

$$CH_3-CH=CH-CH_2-CO-OR$$

where R is hydrogen or alkyl of 1 to 4 carbon atoms, comprising carbonylating butadiene with carbon monoxide and a compound ROH at from 300 to 1,000 bars CO pressure and from 100° to 160° C. in the presence of cobalt catalysts and nitrogen bases, wherein $C_4$ cuts are used as starting materials and a tertiary amine having a $pK_A$ of from 3 to 11 is used as the nitrogen base. The pent-3-enoic acid or alkyl esters produced may be used for the manufacture of adipic acid or its alkyl esters, which compounds are starting materials for the manufacture of nylons.

9 Claims, No Drawings

MANUFACTURE OF PENT-3-ENOIC ACID AND ITS ALKYL ESTERS

This is a continuation of application Ser. No. 805,416 filed Jun. 10, 1977, now abandoned.

The present invention relates to an improved process for the manufacture of pent-3-enoic acid and its alkyl esters, of the general formula I $$CH_3-CH=CH-CH_2-CO-OR \qquad I$$

where R is hydrogen or alkyl of 1 to 4 carbon atoms, by carbonylating butadiene with CO and a compound ROH at from 300 to 1,000 bars CO pressure and from 100° to 160° C. in the presence of cobalt catalysts and nitrogen bases.

Apart from the improvement according to the invention the above process is disclosed in Bulletin of the Chemical Society of Japan 46 (1973), 524–530. However, the process is economically unsatisfactory since pure butadiene has to be used as the starting material. Butadiene however is formed together with other hydrocarbons of 4 carbon atoms when cracking petroleum and can only be isolated therefrom by expensive processes, in the main by extraction. Bearing in mind that the compounds I are intermediates for the manufacture of bulk products, especially plastics, pure butadiene is much too expensive to be considered as an industrial starting material. Carbonlyation of the cheap C₄ cuts has hitherto also been out of the question since the separation of the product mixtures thus obtained causes even greater costs than the production of pure butadiene.

It is an object of the present invention to manufacture pent-3-enoic acid and its alkyl esters by selective carbonylation of the butadiene present in the C₄ cut.

We have found that this object is achieved and that pent-3-enoic acid and its alkyl esters of the general formula I $$CH_3-CH=CH-CH_2-CO-OR \qquad I$$

where R is hydrogen or alkyl of 1 to 4 carbon atoms, are obtained in an elegant reaction, by carbonylating butadiene with CO and a compound ROH at from 300 to 1,000 bars CO pressure and from 80° to 160° C. in the presence of cobalt catalysts and nitrogen bases, by using C₄ cuts as starting materials and a tertiary amine having a $pK_A$ of from 3 to 11 as the nitrogen base.

Under these conditions, the butenes and butynes are, surprisingly, not carbonylated or only carbonylated to a negligible degree and can, after completion of the reaction, simply be vented together with the butanes and used, for example, to manufacture the carbon monoxide.

For the purpose of the invention C₄ cuts are all mixtures of predominantly non-branched hydrocarbons of 4 carbon atoms, which contain more than 10% by weight of buta-1,3-diene (butadiene) and more than 15% by weight of butenes. Depending on their source, the individual components are normally present in the following proportions in such mixtures:

| | | |
|---|---|---|
| butadiene | 10–70, on average | 40–60, % by weight |
| isobutene | 15–40, on average | 20–35, % by weight |
| but-1-ene | 10–40, on average | 10–25, % by weight |
| but-2-ene | 5–20, on average | 5–15, % by weight |
| butanes | 1–10, on average | 1–10, % by weight |
| butynes | 0.1–3, on average | 0.1–3, % by weight |

The mixtures defined, containing, in the extreme case, only 10% of butadiene and 15% of butenes, accordingly are not conventionally encountered in industry but it is not inconceivable that even such mixtures may arise in certain processes. The purpose of the definition is therefore to specify the lower limits for which the process according to the invention can still be regarded as economical.

The presence of the bases defined is essential for the selectivity of the carbonylation of butadiene.

Advantageously, the bases are present during the reaction in an about equimolar ratio to the butenes. Higher concentrations do not provide any economic advantages, whilst at lower concentrations the rate of reaction and selectivity (in respect of butadiene alone reacting) decrease. According to observations to date, it suffices to use 0.5 mole of the base per mole of butenes, but it is preferred to use at least 0.8 mole and preferably 1 mole.

Suitable tertiary amines are, above all, N-heterocyclic compounds, eg. pyridine ($pK_A$ 5.3) and bases related thereto, eg. quinoline ($pK_A$ 4.9), isoquinoline ($pK_A$ 5.4), 2,2'-dipyridil ($pK_A$ 4.1) and the alkyl-, aralkyl- and aryl-substituted derivatives of these bases, eg. 2-picoline ($pK_A$ 5.2), 3-picoline ($pK_A$ 6.0), 4-picoline ($pK_A$ 6.0), 2,3-dimethylpyridine ($pK_A$ 6.6), 2,4-dimethylpyridine ($pK_A$ 7.0), 3,5-dimethylpyridine ($pK_A$ 6.2) and 4-benzylpyridine ($pK_A$ 5.2). Trialkylamines, eg. trimethylamine ($pK_A$ 9.8) and triethylamine ($pK_A$ 11.0), and dialkylarylamines, eg. N,N-dimethylaniline ($pK_A$ 5.2) and N,N-diethylaniline ($pK_A$ 6.6), may also be used. It is preferred to use bases which have a higher boiling point than the products I, so that the latter can readily be distilled from the reaction mixture.

The cobalt catalysts - they are carbonyl complexes, in the main dicobalt-octacarbonyl and cobalt-carbonyl hydrides - are formed under the reaction conditions from cobalt salts, eg. cobalt acetate and cobalt formate, which are generally employed in from 0.2 to 7% strength by weight aqueous or organic solutions or suspensions. However, preferably the pentenoic acid esters are manufactured starting from organic solutions of dicobalt-octacarbonyl. The manufacture of this complex and of its solutions is generally known and therefore does not require special discussion.

The molar ratio of cobalt to butadiene is preferably from 1:25 to 1:200.

Within the stated temperature range of from 80° to 160° C., the best results, from an economic point of view, are obtained at from 100° to 140° C. As regards the carbon monoxide pressure, which is in general from 300 to 1,000 bars, the range from 450 to 900 bars has proved particularly suitable.

Preferably, the process of the invention is used to manufacture the pentenoic acid alkyl esters, and in particular the lowest-boiling ester, i.e. the methyl ester.

In accordance with the carbonylation reaction $$CH_2=CH-CH=CH_2 + ROH + CO \xrightarrow[\text{base}]{CO}$$

$$CH_3-CH=CH-CH_2-COOR$$

the amounts of alcohol required are at least equimolar to the butadiene. Since, however, it is advantageous to carry out the reaction in solution, and this is best done in the alcohol ROH, the alcohol is in practice present in an excess of from 1 to 5 moles.

The manufacture of the acids I (R=H), using water as a reactant in the carbonylation reaction, is, it is true, readily feasible in industrial operation of the process of the invention, but because of the more expensive further processing involved it only offers advantages in special cases. If it is desired to obtain the acids as products, it is advantageous to employ the water required for this purpose in the form of a solution in an aprotic water-soluble solvent, eg. tetrahydrofuran, dioxane, acetonitrile or acetone.

In general, it is advisable to carry out the reaction - which can be carried out batchwise or continuously in accordance with the conventional carbonylation methods - in an organic solvent, the latter being present in from about 0.5 to 2 times the volume of the $C_4$ cut. Suitable solvents, when manufacturing the esters, are above all the alcohols ROH, but also those solvents which have already been mentioned in connection with the manufacture of the acids.

The end of the reaction - after about 1 to 4 hours, depending on the reaction conditions - is readily detectable from the fact that the CO pressure no longer drops or no longer has to be brought back to the chosen value. On letting down the reaction mixture, the unconverted constituents of the $C_4$ cut are evolved first, followed by the low-boiling solvents, the alcohol and, where present, the water. The mixture which remains is then worked up by distillation. The cobalt complex and the bases remain in the bottom product and can be recycled to the carbonylation stage, whilst the esters are rectified. If the amine is more volatile than the products, the working-up must be modified accordingly, in the conventional manner.

The yields of the products are as a rule from 90 to 98%, based on butadiene employed. Where saturated acids of 5 carbon atoms, or their esters, are produced - normally in amounts not exceeding 1% - they do not interfere with the economy of the process according to the invention.

The particularly valuable esters I, and the free acid, can be converted in accordance with the conventional methods of carbonylation or hydroformylation followed by oxidation or hydrogenating amination, respectively into adipic acid or into aminocaproic acid and further into caprolactam. This for the first time provides an economical method of using the cheap $C_4$ cuts to manufacture the valuable nylon intermediates, for the manufacture of which it has hitherto been necessary, as is well known, to start from far more expensive raw materials.

EXAMPLE 1

125 g of a $C_4$ cut of the following composition

| butadiene, | 44% by weight | |
|---|---|---|
| but-1-ene, | 17% by weight | (21 g~0.38 mole) |
| but-2-ene, | 7% by weight | ( 9 g~0.16 mole) |
| isobutene, | 28% by weight | (35 g~0.63 mole) |
| butanes, | 3% by weight | |
| butynes, | 1% by weight | | were carbonylated in a test apparatus at 120° C. and 600 bars CO pressure in the presence of 129 g (1 mole) of isoquinoline, 112 g (3.5 moles) of methanol and 7 g (0.02 mole) of dicobalt-octacarbonyl. The reaction had ceased after about 2.5 hours. The reaction mixture was then let down, so that the unconverted constituents of the $C_4$ cut and the excess methanol were released, and the residue was worked up by distillation in the conventional manner. The catalyst remained in the high-boiling isoquinoline whilst the carbonylation products were distilled off. Fractionation of the latter mixture under atmospheric pressure gave 98% of pent-3-enoic acid methyl ester of boiling point 134° C. and 1% of methyl esters of saturated carboxylic acids of 5 carbon atoms.

EXAMPLE 2

Following the procedure described in Example 1, but with 1 mole of pyridine instead of quinoline, a 96% yield of pent-3-enoic acid methyl ester was obtained.

EXAMPLE 3

Again following the procedure described in Example 1, but with 4-methylpyridine as the tertiary amine and at a carbonylation temperature of 135°-140° C., a 94% yield of pent-3-enoic acid methyl ester was obtained.

EXAMPLE 4

The carbonylation of 125 g of the $C_4$ cut described in Example 1, at 140° C. and 600 bars CO pressure, in the presence of 36 g (2 moles) of water and 79 g (1 mole) of pyridine, gave, after conventional working up of the reaction mixture, a 63% yield of pent-3-enoic acid.

We claim:

1. In a process for the manufacture of pent-3-enoic acid alkyl esters of the formula I $$CH_3-CH=CH-CH_2-CO-OR \qquad I$$

where R is alkyl of 1 to 4 carbon atoms in which butadiene is carbonylated with carbon monoxide and a compound ROH where R is defined as above at from 300 to 1,000 bars carbon monoxide pressure and a temperature of from 80° to 160° C. in the presence of cobalt catalysts and nitrogen bases, the improvement which comprises: using as the butadiene to be carbonylated a $C_4$ hydrocarbon cut containing butadiene, butenes, butynes and butanes and selectively carbonylating butadiene by using as the nitrogen base a tertiary amine having a $pK_a$ of from 3 to 11 in an amount of from about 0.5 to 1 mole of tertiary amine per mole of butenes contained in the $C_4$ cut, whereby the butadiene is selectively reacted whereas the other components of the $C_4$ cut remain essentially unreacted.

2. A process as set forth in claim 1 wherein the $C_4$ cut is made up of the following components:

| butadiene | 10–70%, by weight |
|---|---|
| isobutene | 15–40%, by weight |
| but-1-ene | 10–40%, by weight |
| but-2-ene | 5–20%, by weight |
| butanes | 1–10%, by weight |
| and butynes | 0.1–3%, by weight. |

3. A process as set forth in claim 1 wherein $C_4$ cuts containing from 40 to 60% by weight of butadiene are used.

4. A process as set forth in claim 1 wherein the $C_4$ cut is made up of the following components:

| | |
|---|---|
| butadiene | 40–60%, by weight |
| isobutene | 20–35%, by weight |
| but-1-ene | 10–25%, by weight |
| but-2-ene | 5–15%, by weight |
| butanes | 1–10%, by weight |
| and butynes | 0.1–3%, by weight. |

5. A process as set forth in claim 1 wherein R is methyl.

6. A process as set forth in claim 5 wherein 1 mole of tertiary amine is used per mole of butenes.

7. A process as set forth in claim 6 wherein isoquinoline is used as the tertiary amine.

8. A process as set forth in claim 1, wherein pyridine or isoquinoline is used as the nitrogen base.

9. A process as set forth in claim 1, wherein the temperature is maintained at from 100° to 140° C.

* * * * *

UNITED STATES PATENT AND TRADEMARK OFFICE
CERTIFICATE OF CORRECTION

PATENT NO. : 4,550,195

DATED : October 29, 1985

INVENTOR(S) : Rolf PLATZ et al.

It is certified that error appears in the above—identified patent and that said Letters Patent is hereby corrected as shown below:

On the title page:

Please Add:

[30] Foreign Application Priority Data

July 3, 1976 [DE] Fed. Rep. of Germany...... 2630086

Signed and Sealed this

Twenty-fifth Day of March 1986

[SEAL]

Attest:

DONALD J. QUIGG

Attesting Officer     Commissioner of Patents and Trademarks